US012584914B2

(12) United States Patent
Lous et al.

(10) Patent No.: US 12,584,914 B2
(45) Date of Patent: Mar. 24, 2026

(54) SELF-MIXING INTERFEROMETRY FOR ABSORPTION OR COLOR DETECTION AND APPLICATION IN LATERAL FLOW TESTING

(71) Applicant: ams-OSRAM AG, Premstaetten (AT)

(72) Inventors: Erik Jan Lous, Veldhoven (NL);
Thomas Stockmeier, Premstaetten (AT)

(73) Assignee: AMS-OSRAM AG, Premstätten (AT)

( * ) Notice: Subject to any disclaimer, the term of this patent is extended or adjusted under 35 U.S.C. 154(b) by 553 days.

(21) Appl. No.: 18/005,200

(22) PCT Filed: Jul. 13, 2021

(86) PCT No.: PCT/EP2021/069387
§ 371 (c)(1),
(2) Date: Jan. 12, 2023

(87) PCT Pub. No.: WO2022/013176
PCT Pub. Date: Jan. 20, 2022

(65) Prior Publication Data
US 2023/0266313 A1     Aug. 24, 2023

(30) Foreign Application Priority Data

Jul. 15, 2020     (EP) ..................................... 20186067

(51) Int. Cl.
*G01N 33/543*        (2006.01)
*G01N 21/77*         (2006.01)
*G01N 21/78*         (2006.01)

(52) U.S. Cl.
CPC ....... *G01N 33/54388* (2021.08); *G01N 21/78* (2013.01); *G01N 2021/7759* (2013.01); *G01N 2201/0636* (2013.01)

(58) Field of Classification Search
CPC ............. G01N 33/54388; G01N 21/78; G01N 2021/7759; G01N 2201/0636;
(Continued)

(56) References Cited

U.S. PATENT DOCUMENTS

2005/0036148 A1* 2/2005 Phelan ............... G01N 21/8483
356/446
2008/0102473 A1* 5/2008 Fouquet ............. G01N 21/8483
435/7.1
(Continued)

FOREIGN PATENT DOCUMENTS

CN        108139332  A     6/2018
CN        110806397  A     2/2020
WO      2017162677  A1     9/2017

OTHER PUBLICATIONS

Bhardwaj et al., Compact and self-aligned fluid refractometer based on the Doppler-induced self-mixing effect, Applied Optics, vol. 59, No. 10, Mar. 25, 2020, pp. 3064-3072.
(Continued)

*Primary Examiner* — Dennis White
(74) *Attorney, Agent, or Firm* — MH2 Technology Law Group LLP

(57)     ABSTRACT

It is proposed to use self-mixing interferometry for determining an absorption. The monitoring device for use in lateral flow testing for detecting presence or amount of an analyte in a liquid includes a housing, the housing including a carrier holder for holding a carrier for transport of the liquid; at least a first light source which is a resonant-cavity light source having a cavity; and an evaluation unit, operationally connected to at least the first light source for detecting a measurement signal. The first light source is structured and arranged to illuminate with light a test range in a test area of a carrier held in the carrier holder; and to
(Continued)

couple back into the cavity of the first light source a portion of the light coming back from the test range.

20 Claims, 3 Drawing Sheets

(58) Field of Classification Search
CPC ..... G01N 2021/451; G01N 2021/7773; G01N 21/8483
See application file for complete search history.

(56) References Cited

U.S. PATENT DOCUMENTS

| | | | | |
|---|---|---|---|---|
| 2012/0021531 A1* | 1/2012 | Ellis | ................... | G01N 21/8483 |
| | | | | 422/69 |
| 2018/0149600 A1* | 5/2018 | Farrell | ............ | G01N 33/54373 |

2018/0224378 A1    8/2018   Kay et al.

OTHER PUBLICATIONS

Wang et al., A simple lateral flow biosensor for the rapid detection of copper(II) ions based on click chemistry, RSC Advances, vol. 5, No. 92, 2015, pp. 75722-75727.

Extended European Search Report dated Dec. 16, 2020, EP Application No. 20186067.3, 12 pages.

International Search Report dated Sep. 21, 2021, PCT Application No. PCT/EP2021/069387, 2 pages.

Chinese Office Action issued in corresponding Chinese Patent Application No. 2021800497008 dated Nov. 19, 2025, with English translation, 12 pages.

Dongsheng LAN (Examiner) Chinese Office Action issued in corresponding Chinese Patent Application No. 2021800497008 dated Jan. 21, 2025, with English translation, 11 pages.

* cited by examiner

SELF-MIXING INTERFEROMETRY FOR ABSORPTION OR COLOR DETECTION AND APPLICATION IN LATERAL FLOW TESTING

CROSS-REFERENCE TO RELATED APPLICATIONS

The present application is a national stage entry from International Application No. PCT/EP2021/069387, filed on Jul. 13, 2021, published as International Publication No. WO 2022/013176 A1 on Jan. 20, 2022, and claims priority to EP Application 20186067.3 filed Jul. 15, 2020, the disclosures of all of which are hereby incorporated by reference herein in their entireties.

FIELD OF THE INVENTION

The invention relates to the field of sensing, more particular of optical sensing. More specifically, it relates to ways of detecting or determining absorption or color changes. The invention furthermore relates to an application of the sensing, namely to chemical analysis based on optical properties, in particular based on light absorption properties, and more specifically based on optical and absorption properties, respectively, of a binding partner bonded to an analyte. For example, the sensing can be applied in lateral flow testing. The invention relates to methods and apparatuses according to the opening clauses of the claims.

BACKGROUND OF THE INVENTION

Self-mixing interferometry (SMI) is a known technique. A survey over the technology and its current applications can be found in "Laser feedback interferometry: a tutorial on the self-mixing effect for coherent sensing" by Thomas Taimre et al. (Advances in Optics and Photonics 7, 570-631, 2015). So far, SMI is applied for sensing magnitudes which are related to path length differences, such as for sensing displacement, distance, velocity, flow velocity, refractive index.

SMI is a technique in which a light beam from a resonant-cavity light source is reflected from an object back into the cavity of the light source. The reflected light interacts and in particular interferes with the light inside the light source, more particularly inside the cavity, and this causes changes in the optical and electrical properties of the light source. Information about the object can be obtained by analyzing these. SMI is also known as feedback interferometry, induced-modulation interferometry or backscatter modulation interferometry.

Resonant cavity light sources are, e.g., lasers or resonant-cavity light-emitting diodes (RC-LEDs).

Furthermore, methods are known for detecting an analyte in a sample, wherein the detection is accomplished by detecting changes in color intensity originating from a marker bonded to the analyte. For example, in lateral flow testing (LFT), which in particular can be lateral flow immunochromatographic assay testing, the presence of an analyte (target substance) in a liquid sample is visually detected as follows: The liquid sample is applied to a carrier, such as to a strip, more particularly to a sample pad of the carrier, and runs along the carrier, across a pad referred to as conjugate pad providing the markers which bond to the analyte. Then the liquid runs further to a test area in which analyte bonding agents are fixed to the carrier, such that at least a portion of the analyte stays there instead of continuing running across the carrier. The markers bonded to the analyte, do, when bonded to the analyte bonding agent, show a specific color (first color). Detecting that color means a positive test result: The analyte is contained in the liquid. For control purposes, such as for validation, the carrier can have a control area in which marker bonding agents are fixed to the carrier, such that markers stay there instead of continuing running across the carrier, e.g., in order to be finally taken up by a porous material. The markers, when bonded to the marker bonding agent, also show a specific color (second color). The first and second colors can be equal or different.

In presence of the analyte in the liquid, the test area will show the first color after the liquid had enough time to reach the test area. And the intensity of this color can be indicative of the concentration of the analyte in the liquid sample. When the liquid sample had enough time to reach the control area, it will also show a specific color, namely the second color—which is particularly important in cases where the liquid sample does not contain any of the analyte, namely in order to ensure that the test has generally worked and that it is correct that the test area does not show the first color.

The inventors recognized that SMI can also be used for detecting or determining absorption and, accordingly, also for detecting or determining color intensities and/or changes in color intensities. And further, they recognized that applying SMI in chemistry or biology and in particular in LFT can make possible new sensing or testing devices.

A possible object of the invention is to create new ways of sensing absorption.

A possible object of the invention is to create new ways of detecting color and/or color changes.

Another possible object of the invention is to provide new ways of detecting, in particular optically detecting, substances.

Another possible object of the invention is to provide new ways for detecting, in particular optically detecting, substances in an automated fashion.

Another possible object of the invention is to provide ways for detecting substances in an automated fashion which are particularly cost-efficient.

Another possible object of the invention is to provide ways for detecting substances at a particularly high sensitivity.

Another possible object of the invention is to provide ways for detecting substances in a particularly fast way.

Another possible object of the invention is to provide ways for detecting substances with a particularly good reproducibility.

Another possible object of the invention is to provide devices for detecting substances which are particularly small.

Another possible object of the invention is to provide devices for detecting substances in a particularly energy-efficient way.

Another possible object of the invention is to provide devices for simultaneously detecting a plurality of substances, in particular wherein the substances are located in small spots which are close to one another.

Another possible object of the invention is to provide new ways for sensing absorption in an automated fashion.

Another possible object of the invention is to provide ways for sensing absorption in an automated fashion which are particularly cost-efficient.

Another possible object of the invention is to provide ways for sensing absorption at a particularly high sensitivity.

Another possible object of the invention is to provide ways for sensing absorption in a particularly fast way.

Another possible object of the invention is to provide ways for sensing absorption with a particularly good reproducibility.

Another possible object of the invention is to provide devices for sensing absorption which are particularly small.

Another possible object of the invention is to provide devices for sensing absorption in a particularly energy-efficient way.

Another possible object of the invention is to provide devices for simultaneously sensing absorption in a plurality of small spots which are close to one another.

Further objects and various advantages emerge from the description and embodiments below.

At least one of these objects can be achieved, at least partially, in some implementations of devices and/or methods described in this disclosure.

SUMMARY OF THE INVENTION

As will have become clear, there are various aspects to the invention.

In a first, more general aspect, the invention concerns the application of SMI to absorption sensing and/or to color sensing.

In a second, more specific aspect, the invention concerns the application of SMI to LFT.

The second aspect regards specific embodiments of the first aspect. Therefore, any feature or embodiment described for the first aspect can apply to any embodiment of the second aspect. However, features or embodiments described for the second aspect can apply also to the first aspect, as far as logically possible.

The first aspect can in particular comprise a use of SMI for detecting or determining an absorption. In particular, an absorption (or absorption intensity) can be determined. Based on suitable gauging, absorption can be determined from SMI data. The detection of changes in absorption on the other hand can be easier, as gauging efforts can be reduced.

For example, the use can be a use of SMI for detecting or determining changes in an absorption, more particularly for determining changes in absorption in lateral flow testing.

The use can comprise illuminating a substance with light emitted from a light source, letting the light interact with the substance and coupling a portion of the light having interacted with the substance back into the light source.

For example, the use can comprise detecting or determining the absorption at a specific wavelength, wherein the light emitted from the light source comprises this specific wavelength.

It can be provided that an absorption of a substance is determined, and the light has a wavelength in an absorption band of the substance.

The first aspect can also comprise a use of SMI for detecting a color intensity. Based on suitable gauging, color intensities can be determined from SMI data. The detection of changes in color intensity on the other hand can be easier, as gauging efforts can be reduced.

Usually, there is the following relation between the color intensity and the absorption: The higher the color intensity, e.g., because of a higher concentration of a color-bearing substance, the larger the absorption (in an absorption band of the substance). Therefore, what is herein disclosed regarding detection of color intensities can be applied also to detection of absorption, and vice versa.

Furthermore, a color intensity can detected from detecting an absorption, more particularly an absorption at a wavelength related to the color, in particular at a wavelength complementary to the color.

Similarly, the second aspect can in particular comprise a use of SMI for detecting an absorption (or a color intensity) in lateral flow testing (LFT), and more particularly a change in absorption (or of color intensity) in lateral flow testing. In particular, the absorption and color intensity, respectively, can be an absorption and color intensity of a test area of a carrier of an LFT device. Alternatively or in addition, the absorption and color intensity, respectively, can be an absorption and color intensity of a control area of an LFT device. Yet another alternative or additional possibility is that the absorption and color intensity, respectively, is an absorption and color intensity of a reference area of an LFT device. The reference area will be described further below.

In LFT, a concentration of a color-bearing substance in a test area increases with time, such that a color intensity and a corresponding absorption in a test area increases with time. This can be detected using SMI using light having a wavelength which is absorbed by the substance.

At this point, we shall clarify what using SMI can mean. It can more specifically mean to use a resonant-cavity light source, let light emitted by the light source interact with an object, such as with a substance, and couple a portion of the light having interacted with the object back into a cavity of the light source. This causes changes in the optical and electrical properties of the light source, which can be monitored—by monitoring a corresponding measurement signal. The light coupled back into the cavity can comprise, e.g., light reflected by the substance. It can, in instances, also comprise light having traversed the substance, in particular twice, as explained further below for embodiments in which the device comprises a mirror.

The measurement signal depends on the object (or substance) and more particularly on the color of the object and/or of the absorption properties of the object. The measurement signal can be related to a signal or magnitude which is influenced by interference within the cavity of the light source, between light being generated in the cavity and the light coupled back into the cavity. The measurement signal or, more particularly, an amplitude or intensity thereof can be indicative of an absorption (and of a color) of the object (or substance). More particularly it can be indicative of an amount of absorption having occurred to the light emitted from the light source for illuminating the object (or substance), in particular by the interaction between the light and the object (or substance).

There are at least two measurement signals which can be monitored in order to learn about the object. These measurement signals are the same as known in the art for SMI; cf., e.g., the article by Thomas Taimre et al. mentioned above. It is possible to monitor the light emitted from the light source, and more specifically an intensity of the light emitted from the light source. This can be accomplished, e.g., by means of a photodetector. E.g., stray light or a portion of light coupled out of the light beam emitted from the light source, e.g., by a beam splitter, can be monitored. However, this requires the provision of a light detector.

A more simple way is to monitor an electrical supply signal feeding the light source. The light source can be powered by a supply signal, such as by a supply voltage or a supply current. The supply signal is applied to supply terminals of the light source, such that the measurement signal can be measured, e.g., at the supply terminals. The measurement signal can thus be, e.g., a voltage or a current present at the supply terminals of the light source, or can be an impedance of the light source.

In contrast to SMI measurements in prior art, where the number of minima and/or maxima (originating from interference) is counted and evaluated, it is herein proposed to monitor an intensity (optical) and an amplitude (electrical) and/or a phase (electrical), respectively, associated with the light source (and influenced by the interference); wherein, e.g., an impedance (electrical) can be monitored.

In particular, the measurement signal can be time-averaged in order to remove fast changes which are unrelated to the monitored region and to the object or substance, respectively. E.g., vibrations can be averaged out this way. For example, the measurement signal can be time-averaged over durations between 1 s and 20 s.

Furthermore, corrugations of the carrier (in the illuminated region, e.g., in the test region) and irregularities or inhomogeneities of the carried can influence the measurement and thus degrade the quality of measurement results. This problem can be mitigated by illuminating a relatively large range of the carrier, in other words by a kind of spatial averaging. Further below, specific embodiments are described which can be particularly suitable in this regard, e.g., in which a lens is used for producing parallelized light for illuminating the object (or substance). E.g., the light beam emitted from the light source can be widened this way.

A way of at least partially understanding the physical origin of the measurement signal is the following (assuming, in this case that the light source is a laser): The coupled-back light changes the laser threshold condition, which again changes the carrier density $N=N(\phi)$, $\phi$ designating the interferometric phase. A consequence thereof is a change of the electrical supply signal, more particularly of the supply voltage applied to the laser, because $V=V(N(\phi))$, thus the measurement signal can be obtained from the supply voltage. And another consequence thereof is a change of the emitted optical power P, because $P=P(N(\phi))$, thus the measurement signal can be obtained from light intensity measurements, e.g., by means of a photodiode.

Examples for resonant-cavity light sources are lasers and RC-LEDs. For creating interference in the light source and more particularly in the cavity of the light source, it is advantageous to have a notable coherence length of the light from the light source. From this point of view, a laser, usually having a very large coherence length, is prone to provide stronger measurement signals than an RC-LED which usually has rather small coherence lengths only. However, both can be used as a light source.

In particular, light sources can be considered for use which are resonant-cavity light sources having a coherence length which is longer than the length of the cavity of the light source.

In order to adjust the intensity ratio of light coupled out of the light source to the intensity of light coupled into the light source, a transmission of an end mirror of the light source can be adjusted or be selected suitably.

In particular, vertical-cavity surface-emitting lasers (VCSELs) and edge-emitting lasers (EELs) can be particularly suitable light sources. They can be very small.

Regarding the wavelength of the light emitted from the light source, it is preferably a wavelength within an absorption band of a substance or color to be investigated. E.g., if a substance (or object) is investigated having an absorption band in the visible part of the spectrum, e.g., in the blue range, such as around 470 nm, the light from the light source should have a wavelength close to 470 nm, too. This way, higher intensities of the measurement signal can be achieved.

A method according to the first aspect can be a method for detecting or determining an absorption in a test range, wherein the method comprises illuminating the test range with light emitted from a resonant-cavity light source having a cavity;

coupling back into the cavity, light coming back from the test range;

thereby producing a change in a generation of light in the light source, in particular due to interference between the coupled-back light and light being generated in the light source;

monitoring a measurement signal of the light source related to the change.

As usual in SMI, the light interacts with an object (or with a substance) present in the test range, and a portion of the light having interacted with the object (or with the substance) is coupled back into the cavity of the light source, more particularly back into a cavity of the light source. The light coupled back into the cavity can comprise light reflected from the object (or substance). An absorption of the object (or substance) can be determined. The absorption can be related to or indicative of a concentration of the substance in the test range.

Likewise, another method according to the first aspect can be a method for detecting or determining a color intensity in a test range, wherein the method can otherwise be identical to the described method for detecting or determining an absorption in a test range.

In consideration of color-bearing objects and substances, respectively, yet another method according to the first aspect can be a method for detecting presence or amount of a substance in a test range. Also this method can in particular comprise the same method steps as the described method for detecting or determining an absorption in a test range.

From the monitoring of the measurement signal, the absorption and/or the color intensity and/or the presence or amount of the substance in the test range, respectively, can be determined.

The device according to the first aspect can be a device for detecting or determining an absorption in a test range. And it can also be (cf. above) a device for detecting or determining a color intensity in a test range and also a device for detecting presence or amount of a substance in a test range. In all of the three cases, the device comprises a resonant-cavity light source for illuminating the test range with light, wherein the light source, and in particular its outcoupling mirror, is suited for coupling back into the a cavity of the light source light coming back from the test range;

an evaluation unit for monitoring a measurement signal of the light source related to changes in a generation of light in the light source originating from interference between the coupled-back light and light being generated in the light source.

With reference to the above, the evaluation unit can monitor an intensity or amplitude of the measurement signal, which is related to the amount of substance or substance concentration in the test range, due to the amount of absorption by the substance.

Turning now to the second aspect again. The monitoring device according to the second aspect can be a monitoring device for use in lateral flow testing—in particular wherein in the lateral flow testing, presence or amount of an analyte in a liquid is detected. The device can comprise a housing, the housing comprising a carrier holder for holding a carrier, in particular for holding a carrier for transport of the liquid;

at least a first light source which is a resonant-cavity light source having a cavity;

an evaluation unit which is operationally connected to at least the first light source, for detecting a measurement signal and optionally also for evaluating the measurement signal;

wherein the first light source is structured and arranged to illuminate with light a test range in a test area of a carrier held in the carrier holder; and to couple back into the cavity of the first light source a portion of the light coming back from the test range.

The light coming back from the test range can in particular comprise light reflected back from the test range.

The measurement signal can be a signal depending on interference taking place in the cavity between the coupled-back light and light being generated in the light source and being present in the cavity, respectively.

The measurement signal can be a signal depending on the coupling-back of the light.

The amount of light coupled back into the cavity of the first light source depends on the amount of substance (analyte) in the test range.

In some embodiments, the evaluation unit comprises an optical detector for detecting an intensity of light emitted by the light source. In particular, the measurement signal can be derived from the optical detector. E.g., the detected intensity can be evaluated by the evaluation unit and can be related to an amount of the analyte present in the liquid.

In some embodiments, the evaluation unit comprises an electrical detector for detecting an electrical supply signal feeding the light source, in particular wherein the measurement signal is derived from the electrical detector. E.g., the detected electrical supply signal can be evaluated by the evaluation unit and can be related to an amount of the analyte in the liquid.

For example, the first light source can be supplied with a constant voltage, and the current can be used as the measurement signal. Or, in another example, the first light source can be supplied with a constant current, and the voltage can be used as the measurement signal. Or, in yet another example, an impedance of the first light source can be determined from current and voltage of the supply signal and can be used as the measurement signal.

At least the first light source can be disposed in the housing, in particular, it can be fixed to a portion of the housing.

In some embodiments, the housing comprises a compartment in which at least the first light source is disposed. In particular, said compartment can be designed to impede that light from outside the housing reaches the test range of a carrier when the carrier held in the carrier holder.

In some embodiments, the monitoring device further comprises a mirror disposed in the housing, in particular fixed to a portion of the housing. The mirror can be arranged and aligned to reflect light emitted from the first light source having traversed a carrier held in the carrier holder back to the carrier to traverse the carrier again. A portion of the light can then be coupled back into the cavity of the light source.

This way, light can traverse the carrier, more particularly the test area, twice, thus undergoing an increased absorption. An increased sensitivity at low analyte concentrations can be achieved this way.

Of course, to make use of this effect, a carrier should be used which is at least partially transparent for the light emitted from the first light source.

E.g., the mirror can arranged such that, when a carrier is held in the carrier holder, the carrier is arranged between the mirror and the first light source. The mirror and more particularly its reflective side, can face the carrier.

In some embodiments, the mirror is a flat mirror.

In some embodiments, the mirror is a curved mirror, e.g., a convex mirror. This can contribute to focusing light back into the cavity.

In some embodiments, the monitoring device further comprises at least a first lens disposed in the housing. It can be fixed to a portion of the housing and/or be fixed to the first light source. This can provide improved stability. The first lens can be arranged on an optical path of the light emitted from the first light source towards a carrier held in the carrier holder, namely between the first light source and a carrier held in the carrier holder.

E.g., the first lens can be arranged such that, when a carrier is held in the carrier holder, the first lens is arranged between the carrier and the first light source.

In some embodiments, the first lens is structured and arranged for producing from the light emitted from the first light source a parallelized light beam. For example, the first light source can emit the light through a first end mirror (first end reflector, or outcoupling mirror) of the cavity, and the lens can be a convex lens which is arranged at a distance from the first end mirror corresponding to a focal length of the first lens.

In some embodiments, the first lens is structured and arranged for producing from the light emitted from the first light source a beam having a beam cross-sectional area exceeding a beam cross-sectional area which a beam of the light emitted from the first light source has when impinging on the first lens.

In some embodiments, the first lens is structured and arranged for producing from the light emitted from the first light source a beam having a beam cross-sectional area which is smaller than a beam cross-sectional area which a beam of the light emitted from the first light source has when impinging on the first lens.

In some embodiments, the first lens is structured and arranged for focusing the light emitted from the first light source.

In particular, the first lens can be structured and arranged for focusing the light emitted from the first light source onto the test area.

This way, an increased light intensity on the test area can be achieved. And it is possible this way to work with a very small test range, e.g., enabling investigating of a high number of analytes within a relatively small test range (and small test regions).

In some embodiments, the monitoring device further comprises a printed circuit board held by the housing, on which at least the first light source is mounted. In particular, the printed circuit board can be aligned parallel to a carrier when the carrier is held in the carrier holder. More particularly, the printed circuit board can be aligned parallel to a surface of a carrier when the carrier is held in the carrier holder, still more particularly wherein said surface faces the printed circuit board.

At least a portion of the printed circuit board or the printed circuit board in full can be disposed inside the housing. In some embodiments, a portion of the printed circuit board extends outside the housing.

The monitoring device can comprise an interface, e.g., an interface between the monitoring device and an external device, such as to an external processing unit or a mobile computing device such as a smart phone. The interface can be an electrical interface, e.g., a digital interface. It can be a wire-bound interface. In other embodiments, it is a wireless interface.

For example, the monitoring device can be connected to a reader by means of the interface.

The interface can improve automatization.

For example, the monitoring device can be connected to an external device for one or more of providing a supply signal, such as a supply voltage, for the light source(s);
    providing a supply signal, such as a supply voltage, for all components mounted on the printed circuit board;
    detecting and/or evaluating the measurement signal(s).

In some embodiments, said portion of the printed circuit board extending outside the housing can provide said interface. This can make the device particularly compact.

For example, the monitoring device can be operable to communicate the measurement signal and/or results of the evaluation, such as a result of the lateral flow testing, via the interface.

In this regard it shall be mentioned that the evaluation unit does not necessarily need to be comprised in the monitoring device. And it can, but needs not be attached to or disposed in the housing.

For example, by means of the interface, the monitoring device can be operationally connected to an external device in which the evaluation unit is implemented or in which an evaluation of the measurement signal is accomplished.

In some embodiments, the monitoring device further comprises a second light source, in particular wherein the second light source is structured and arranged to illuminate with light a control range in a control area of a carrier held in the carrier holder; and
    to couple back into the cavity of the second light source a portion of the light coming back from the control range.

It can furthermore be provided that the second light source is operationally connected to the evaluation unit for detecting a measurement signal which shall be referred to as control measurement signal.

It is alternatively also possible to use the first light source also for this. For example, it is possible to alternatingly illuminate the control range and the test range by means of the first light source, e.g., in a time-multiplexed fashion. And/or one can alternatingly couple back light into the cavity of the first light source which comes back from the test range and which comes back from the control range, respectively, e.g., in a time-multiplexed fashion. This can be implemented in a straight-forward fashion, e.g., using light guides and switchable beam splitters.

The function of the control area is described elsewhere in this application.

In some embodiments, the monitoring device further comprises a third light source, in particular wherein the third light source is structured and arranged to illuminate with light a reference range in a reference area of a carrier held in the carrier holder; and
    to couple back into the cavity of the third light source a portion of the light coming back from the reference range.

This can be useful for further calibration.

It can furthermore be provided that the third light source is operationally connected to the evaluation unit for detecting a measurement signal which shall be referred to as reference measurement signal.

It is alternatively also possible to use the first light source (or the second light source) also for this. For example, it is possible to alternatingly illuminate the reference range and the test range by means of the first light source or to alternatingly illuminate the reference range and the control range by means of the second light source, e.g., in a time-multiplexed fashion. And/or one can alternatingly couple back light into the cavity of the first light source which comes back from the test range and which comes back from the reference range, respectively; or
    couple back light into the cavity of the second light source which comes back from the control range and which comes back from the reference range, respectively;

e.g., in a time-multiplexed fashion. This can be implemented in a straight-forward fashion, e.g., using light guides and switchable beam splitters.

Similarly, the first light source can be used in an analogous fashion for implementing the functions of the first, the second and also the third light source.

In other words:

In some embodiments, the second light source is identical to the first light source.

In some embodiments, the third light source is identical to the second light source.

In some embodiments, the second light source and the third light source are both identical to the first light source.

The reference area will be explained below.

Analogously to what is herein described for the first lens with respect to the first light source, a second lens and/or a third lens can be provided in conjunction with the second and third light source, respectively, showing analogous features.

In some embodiments, the monitoring device further comprises a further first light source. This further first light source can in particular be structured and arranged to illuminate with light a further test range in the test area of a carrier held in the carrier holder; and
    to couple back into the cavity of the further first light source a portion of the light coming back from the further test range.

This can make possible, e.g., to detect two different analytes in a single test involving a single carrier, as will be explained further below. Similarly, one or more still further first light sources can be provided for testing for still more analytes.

And analogously, also one or more further second light sources can be provided.

And analogously, also one or more further third light sources can be provided.

Due to the small dimensions of available light sources and enabled by the possibility to limit the illumination of the carrier by the respective light sources to small spots (the "ranges" being laterally small), testing (parallel testing) for different analytes on one and the same carrier using one and the same lateral flow testing device is possible, even without overly enlarging a width of the carrier. In particular, VCSELs and EELs and RC-LED can be suitable for this.

The lateral flow testing device according to the second aspect can comprise a monitoring device as herein described and a carrier held in the carrier holder. The carrier can in particular comprise a sample pad for application of the liquid;
    a conjugate pad providing markers for marking the analyte by bonding to the analyte;

a test area in which analyte bonding agents for specifically bonding to the analyte are fixed to the carrier;

a control area in which marker bonding agents for bonding to the markers are fixed to the carrier.

The carrier can in particular be structured such that the liquid is transported, in particular transported by capillary forces, from the sample pad to the conjugate pad, thereafter to the test area and thereafter to the control area.

In some embodiments of the lateral flow testing device, the carrier further comprises a reference area which is void of bonding agents fixed to the carrier, in particular void of analyte bonding agents and void of marker bonding agents.

The reference area can be very useful for calibration purposes. When the liquid wets the carrier, optical properties such as reflectivity of the carrier can change, which again can and usually will result in changes in the measurement signal. Illuminating the reference area and coupling back the light into the cavity of, e.g., the third light source, makes possible to derive a reference measurement signal which can provide useful information for interpreting the measurement signal (from the test range). For example, the measurement signal can be evaluated in dependence of the reference measurement signal. In a simple case, e.g., for the evaluation, a difference between the measurement signal and the reference measurement signal can be determined.

In some embodiments, the reference area is located (with respect to a flow direction of the liquid) between the sample pad and the conjugate pad. The reference area can be downstream of the sample pad and upstream of the conjugate pad.

In some embodiments, the reference area is located (with respect to a flow direction of the liquid) between the conjugate pad and the test area. The reference area can be downstream of the conjugate pad and upstream of the test area.

In some embodiments, material properties of the carrier are nominally identical in the test area and in the reference area.

In some embodiments, material properties of the carrier are nominally identical in the control area and in the reference area.

In some embodiments, material properties of the carrier are nominally identical in the control area, in the reference area, and in the test area.

These embodiments can contribute ti an improved comparability of the reference measurement signal with the measurement signal and/or the control measurement signal, thus enabling more precise and/or reliable result.

In some embodiments, the carrier is a strip.

In some embodiments, the carrier can be strip-shaped.

In some embodiments, the carrier is operable to transport the liquid. In particular, each of the pads and areas is capable of transporting the liquid.

In some embodiments, the carrier is a carrier of a semiconductor material, in particular wherein the semiconductor material is microstructured, e.g., etched.

In some embodiments, the carrier is a carrier of a glass material, in particular wherein the glass material is microstructured, e.g., etched.

In some embodiments, the carrier is a carrier of a polymer, in particular wherein the polymer is microstructured.

In some embodiments, the carrier is a carrier of a fibrous material, in particular of a paper.

In some embodiments, the carrier comprises a mirror. The mirror can comprise, in particular be, a reflective coating. For example, the carrier, when held in the carrier holder has a first face facing the first light source and/or the printed circuit board, and a second face which is opposite the first face, and the mirror is present on that second face.

This can be an alternative to the described embodiment in which a mirror is a constituent of the monitoring device. And it can serve the same purposes.

In some embodiments, the liquid is a body liquid, in particular a human body liquid. E.g., the liquid can be urine or blood.

In some embodiments, namely in particular for parallel testing, the lateral flow testing device is a lateral flow testing device for detecting presence or amount of an analyte and of a further analyte in a liquid. And the conjugate pad can provide further markers for marking the further analyte by bonding to the further analyte;

the test area can comprise a test region in which the analyte bonding agents for specifically bonding to the analyte are fixed to the carrier, and comprise a further test region in which further analyte bonding agents for specifically bonding to the further analyte are fixed to the carrier;

the control area can comprise a control region in which the marker bonding agents for bonding to the markers are fixed to the carrier, and comprise a further control region in which further marker bonding agents for bonding to the further markers are fixed to the carrier.

Furthermore, the test range is located in the test region; and the lateral flow testing device comprises a second light source which is a resonant-cavity light source and has a cavity. It can be identical with or different from the first light source, and it can be structured and arranged to illuminate with light a control range in the control region; and to couple back into the cavity of the second light source a portion of the light coming back from the control range.

The lateral flow testing device can further comprise a further first light source and a further second light source, both being resonant-cavity light sources and having a cavity each. The further second light source can be identical with or different from the further first light source. The further first light source is structured and arranged to illuminate with light a further test range in the further test region; and to couple back into the cavity of the further first light source a portion of the light coming back from the further test range.

The further second light source is structured and arranged to illuminate with light a further control range in the further control region; and to couple back into the cavity of the further second light source a portion of the light coming back from the further control range.

It can be provided that the second light source, the further first light source and the further second light source are operationally connected to the evaluation unit. This way, measurement signals from all the light sources can be determined and, optionally, also evaluated by the evaluation unit. The presence or amount of two substances (analytes) can thus be detected.

Obviously, it is straight forward to extend this to more than two different analytes, such as to a 3 times 3 matrix of test ranges and, optionally, also of control ranges.

It can be provided that each of the light sources (first, and as far as present, second, third, further first and further second light source) emits the light through a first end mirror (outcoupling mirror) of its respective cavity.

In some embodiments, a distance between the respective end mirror and the carrier (more particularly a surface of the carrier facing the respective end mirror) is between 0.05 mm and 10 mm, more particularly between 0.1 mm and 5 mm.

In some embodiments, the ranges (test range and, as far present, control range, reference range, further test range, further control range) each have an area of between 0.2 mm² and 8 mm, in particular between 0.5 mm² and 4 mm.

The method according to the second aspect can be a method for detecting presence or amount of an analyte in a liquid by lateral flow testing. The method can comprise illuminating a test range in a test area of a carrier with light from a first light source which is a resonant-cavity light source having a cavity;

coupling back into the cavity of the first light source a portion of the light coming back from the test range;

detecting a measurement signal by means of an evaluation unit which is operationally connected to the first light source.

In some embodiments, the carrier comprises a sample pad;

a conjugate pad providing markers for marking the analyte by bonding to the analyte;

a test area in which analyte bonding agents for specifically bonding to the analyte are fixed to the carrier;

a control area in which marker bonding agents for bonding to the markers are fixed to the carrier; and the method comprises letting the carrier transport the liquid from the sample pad to the control area, in particular by capillary forces;

applying the liquid to the sample pad;

letting the markers bond to the analyte at the conjugate pad;

letting the analyte bonding agents bond to the analyte at the test pad;

letting the marker bonding agents bond to the markers at the control area.

In some embodiments, with respect to the direction of flow of the liquid, the conjugate pad is downstream from the sample pad, the test area is downstream from the conjugate pad, the control area is downstream from the test area.

In some embodiments, the method further comprises illuminating a control range in the control area with light from a second light source which is a resonant-cavity light source having a cavity; and coupling back into the cavity of the second light source a portion of the light coming back from the control range;

wherein the second light source is operationally connected to the evaluation unit for detecting a control measurement signal by means of an evaluation unit.

In some embodiments, the carrier comprises a reference area which is void of bonding agents fixed to the carrier, and the method further comprises illuminating a reference range in the reference area with light from a third light source which is a resonant-cavity light source having a cavity; and coupling back into the cavity of the third light source a portion of the light coming back from the reference range;

wherein the third light source is operationally connected to the evaluation unit for detecting a reference measurement signal by means of an evaluation unit.

The method can in particular comprise evaluating by means of the evaluation unit the measurement signal in dependence of the reference measurement signal.

Jointly evaluating the measurement signal and the reference measurement signal can improve results, because changes in reflectivity due to the liquid can be monitored and considered, as announced above already.

We note that it is possible to carry out the methods while the test area is still wetted by the liquid. And it is also possible to carry out the methods while the liquid is still flowing (being transported by the carrier). However, it is also possible to carry out the methods after the liquid has left the test area, such as by evaporation. In this case, reference measurement signals can be used as a reference for the measurement signals. E.g., the evaluation unit can jointly evaluate the reference measurement signals and the measurement signals, e.g., in order to determine the absorption.

Furthermore, it is noted that generally, the provision of a control area is an option. Thus, the described methods and devices can also be implemented without a control area, and, of course, then also without the associated features and parts, such as the second light source.

The invention, in particular its second aspect, can be applied for detecting bio-molecules, such as, e.g., viruses. In such a case, for example, a marker can be a bio-diagnostic color label, such as an antibody conjugated to a coloring particle or molecule, such as a latex ball or a gold nanoparticle; and the analyte bonding agent can be an antibody (fixed to the carrier in the test area), and the marker bonding agent can be another antibody (fixed to the carrier in the test area).

It is noted that in both aspects of the invention and thus for that for the herein described methods and apparatuses, it is possible to accomplish the illumination in a pulsed fashion. And in particular, it can then be provided to detect the measurement signal synchronously to the illumination, such as in a pulsed fashion simultaneously with the illumination.

It is noted that in both aspects of the invention and thus for that for the herein described methods and apparatuses, the sample (liquid; substance) can be still (in the sense of not-moving, stagnant) during the illumination. And in case the sample flows during the illumination, an illumination direction along which the illumination takes place can be perpendicular to a flow direction of the sample.

And, for the herein described methods and apparatuses, a direction of flow of the sample (liquid; substance)—if the sample flows at all —, can be aligned parallel to the test range.

From the paper "Compact and self-aligned fluid refractometer based on the Doppler-induced self-mixing effect" by Vibhor Kumar Bhardwaj and Surita Maini (Applied Optics Vol. 59, No. 10/1 Apr. 2020), a refractometer is known in which SMI technology is used. In contrast thereto, the herein described apparatuses and methods do not include a refractometer or refractometric measurements. And, while in said paper, Doppler shifts are determined, and the investigated fluid has to flow at a non-zero flow rate which should be constant (during the measurements), and an illumination direction along which the sample is illuminated for the Doppler-based measurements should be close to parallel to a flow direction of the sample, for the herein described apparatuses and methods one or more of following applies:

they do not include a determination of a Doppler shift;

the sample may or may not flow;

the sample may flow at an ill-defined flow rate;

a flow rate of the sample may (considerably) vary during the measurement;

the sample may flow along a flow direction which is substantially perpendicular to an illumination direction along which the sample is illuminated with the light.

And the herein described apparatuses and methods do not include determining (or do bit include sensing means for determining) a frequency shift (such as a Doppler shift/flow rate induced frequency shift) of the light coupled back into the cavity of the light source.

A measurement signal detected by a herein-described apparatus or in a herein-described method can be essentially independent of a flow rate the sample may have.

As will be readily understood, features mentioned herein with respect to a method can analogously apply for a described device or use as well. And, similarly, features mentioned herein with respect to a device can analogously apply for a described method or use as well. And, similarly, features mentioned herein with respect to a use can analogously apply for a described method or device as well. The achievable effects correspond to each other.

Further embodiments and advantages emerge from the following description and the enclosed figures and from the dependent claims.

BRIEF DESCRIPTION OF THE DRAWINGS

Below, the invention is described in more detail by means of examples and the included drawings. In the drawings, same reference numerals refer to same or analogous elements. The figures show.

DETAILED DESCRIPTION

The described embodiments are meant as examples or for clarifying the invention and shall not limit the invention.

Figure 1:
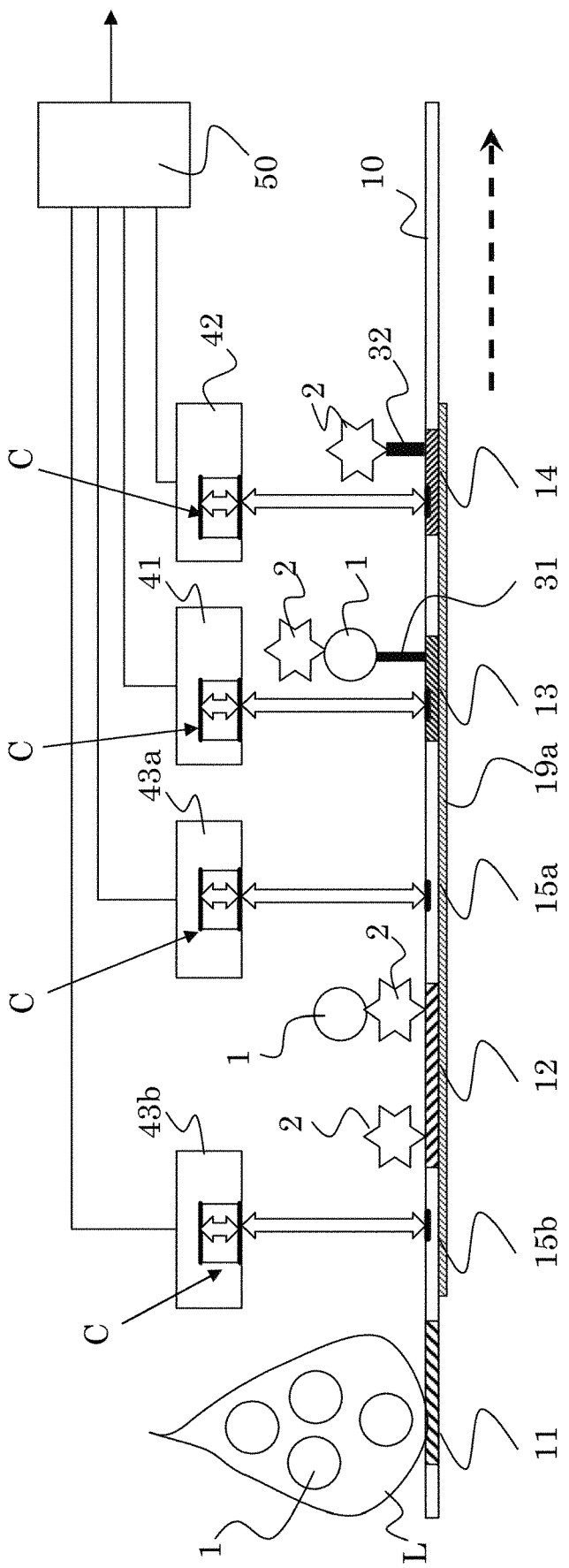
FIG. 1 a very schematic illustration of a side view of an LFT device implementing SMI for detection.

FIG. 1 shows a schematic illustration of a side view of an LFT device implementing SMI for detection. This figure emphasizes the LFT aspect and the related method, and therefore some details, such as a housing of the device are not illustrated in FIG. 1.

A carrier 10 inserted in the device comprises a sample pad 11, a conjugate pad 12, a test area 13 and an optional control area 14. It further comprises two reference areas 15a, 15b, which are generally optional, and wherein a single reference area can be, in instances, sufficient.

A liquid L representing a sample is applied to the sample pad 11. From there, it is transported by the carrier 10, e.g., by capillary forces, along a transport direction illustrated in the figures by the thick dashed arrow. The liquid L can (and in the illustrated case does) contain an analyte 1, such as a virus.

On the conjugate pad 12, markers 2 are present which can bond to the analyte 1. The particles formed this way, when reaching the test area, can bond to analyte bonding members 31 which are fixed to the carrier 10 in the test area 13. Accordingly, a concentration of the particles can increase there with time. The particles bonded to the analyte bonding agents 31 show a specific color, such that an intensity of the color can increase with time and concentration of the bonded particles in the test area 13. This can be detected by detecting absorption, in particular at a wavelength of an absorption band of the bonded particles.

Markers 2 not bonded to the analyte 1 are further transported to the control area 14 and can bond to marker bonding members 32 which are fixed to the carrier 10 in the control area 13. The markers 2 bonded to the marker bonding agents 32 also show a specific color, such that an intensity of that color can increase with time and concentration of these bonded particles in the control area 14.

The detection of the presence and/or the concentration of the respective bonded particles is accomplished using SMI. Due to the colors, an absorption can be detected, wherein the absorption depends on the presence and/or the concentration of the respective bonded particles.

Therefore, the device comprises one or more light sources; in the illustrated example, four light sources 41, 42, 43a, 43b are shown. They are all resonant-cavity light sources comprising a cavity C. Each cavity C has two end mirrors, one of which is the outcoupling mirror from which the respective light source emits light. Light produced in the light source circulates in the cavity, resonating therein. The hollow arrows in the figures symbolize light.

Light emitted from the respective light source illuminates a respective range of the carrier 10 in the respective area 13, 14, 15a and 15b, respectively. These ranges are symbolized by short thick lines in FIG. 1.

A portion of the light is reflected back into the cavity C of the respective light source. Some of the light is, however, absorbed, in particular by the respective bonded particles in the test area 13 and in the control area 14.

Light re-entering the cavity C can influence the light generation in the light source, in particular due to interference with light present in the cavity, i.e. with light being produced in the light source. A notable coherence length of the light can therefore be advantageous. For example, lasers, e.g., VCSELs and EELs can be used. But also RC-LED can be used.

This influence on the light generation can be detected, e.g., from monitoring a supply signal applied to the respective light source. As illustrated in FIG. 1, each of the light sources is operationally connected to an evaluation unit 50 which can be comprised in the device or can be a separate unit. For example, the supply signals are provided by and monitored by the evaluation unit 50. In one example, the current drawn by a light source at a constant supply voltage can be a measurement signal which is related to the influences to the light generation in the light source and thus to the absorption.

The reference measurement signals from the reference areas 15a, 15b (or one of them) can be used for calibration purposes, e.g., for monitoring the effect of a wetting of the carrier 10 by the liquid L. This can lead to more precise and/or more reliable results.

But also when the liquid has left the carrier (or at least the respective regions 13, 14, 15a, 15b), the reference measurement signals from the reference areas 15a, 15b (or from one of them) can be used for calibration purposes, namely in order to compare absorption at an area (15a; 15b) without the color-bearing particles bonded to the carrier 10 to absorption at an area (13; 14) where the color-bearing particles are bonded to the carrier 10 (at least in case of presence of analyte 1 and/or markers 2).

An optional mirror 19a is illustrated in FIG. 1 which can be, e.g., a reflective coating on one side of the carrier 10. This can increase absorption, because the light, after emission from the light source, can pass through the carrier a first time, can then be reflected by the mirror 19a and can the pass through the carrier a second time before possibly entering the cavity C again.

Figure 2:
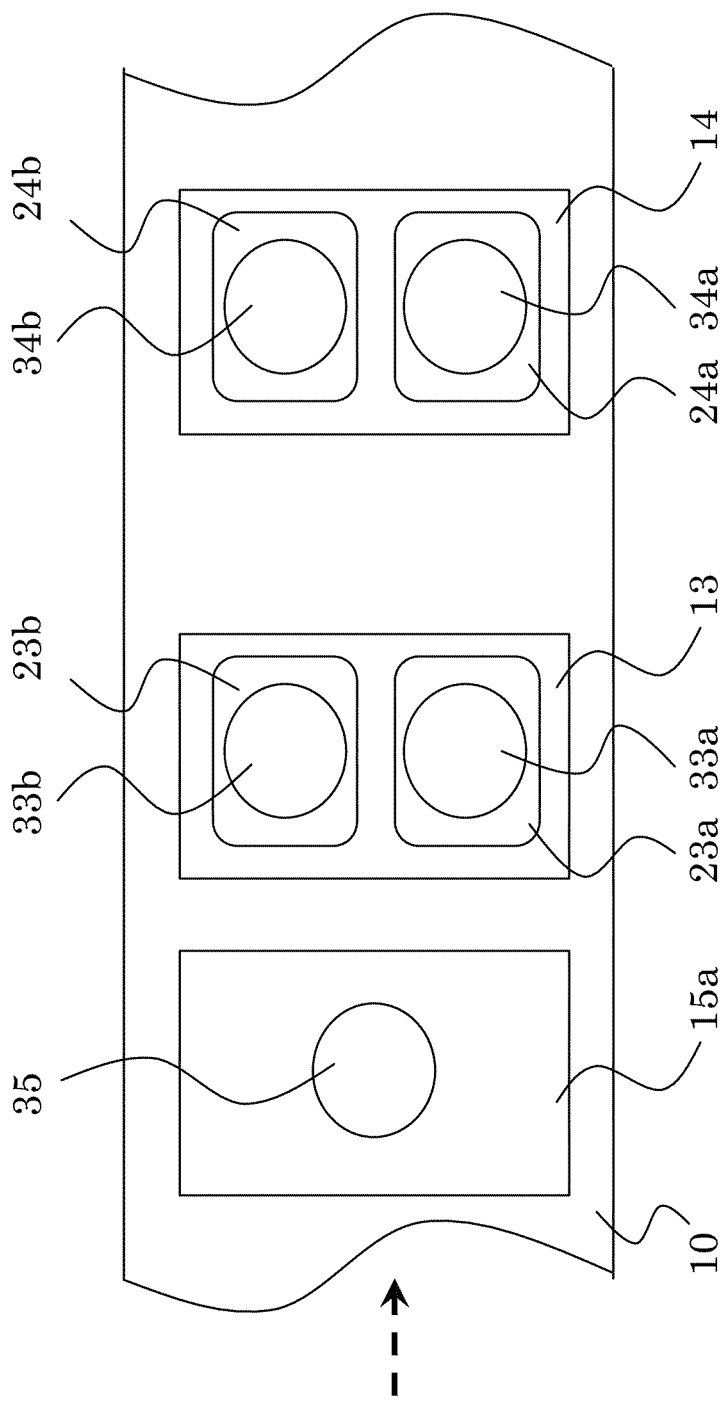
FIG. 2 a very schematical illustration of a top view onto a portion of a carrier.

The method and device can also be applied for simultaneous detection of two or more analytes. FIG. 2 shows a schematical illustration of a top view onto a portion of a carrier 10 which is prepared for detection of two analytes.

The test area 13 comprises two test regions 23a, 23b in which different analyte bonding agents are fixed to the carrier 10, each specific to the respective analyte. Analogously, also the control area 14 comprises two control regions 24a, 24b in which different member bonding agents are fixed to the carrier 10, each specific to the respective marker.

For each of the regions, a separate light source can be provided, illuminating a respective range 33a, 33b, 34a and 34b, respectively.

As illustrated in FIG. 2, it can be sufficient to implement only one light source for illuminating only one reference range 23 (e.g., in a reference area 15a). However, since the wavelengths for probing the different test regions 23a, 23b can be different, it can be of advantage to use two light sources for illuminating two reference ranges (not shown in FIG. 2) in order to achieve an even better evaluation and/or calibration.

Since very small light sources can be used here, it is possible to detect a relatively high number of different analytes while using up only a relatively small surface area of the carrier 10, thus enabling small carriers and small devices.

Figure 3:
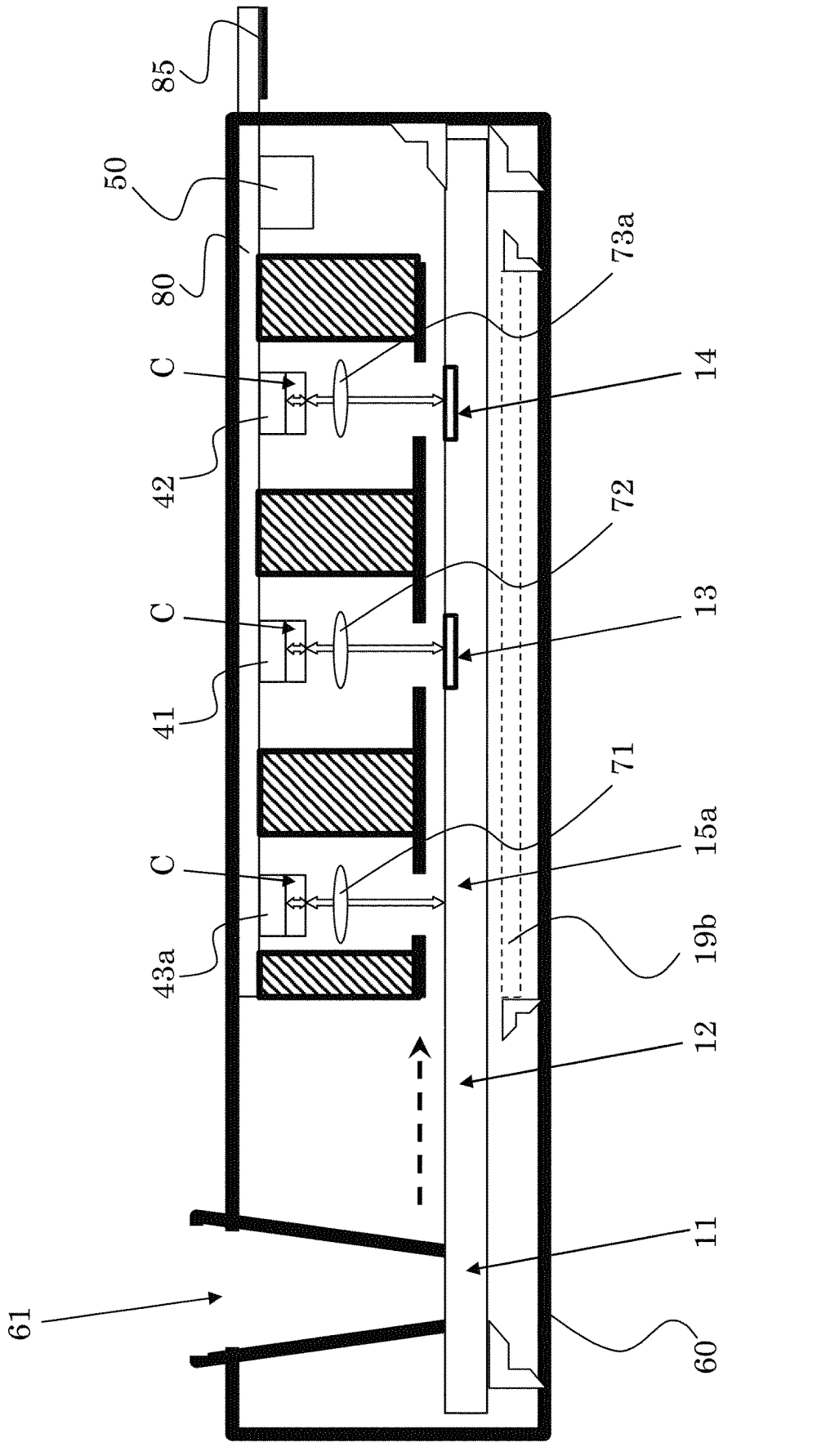
FIG. 3 a very schematic illustration of a side view of an LFT device implementing SMI for detection.

FIG. 3 shows a schematic illustration of a side view of an LFT device implementing SMI for detection. Most details have been described already in conjunction with FIG. 1. Accordingly, it is referred to above for that.

The device comprises a housing 60 and a sample inlet 61. The housing 60 comprises several baffles (thick lines or hatched in FIG. 3) to keep ambient light out of the housing and in particular away from the ranges (test range, control range, reference range). Also the sample inlet can serve as such a baffle.

The carrier 10 is held by a carrier holder (symbolized by the large angles in FIG. 3).

Furthermore, as an option, a mirror 19b is disposed in the housing 60, for the described purpose.

For each light source, a lens 71, 72, 73a is provided, disposed in the light path between the respective light source and the carrier 10. This way, the light beam exiting the respective light source can be, e.g., widened and/or parallelized. The lenses can optionally be attached to the respective light sources.

The device further comprises a printed circuit board 80 on which the light sources are mounted. The device can also comprise an interface 85 which can be implemented at or by the printed circuit board 80. The interface 85 can, as illustrated, be comprised in a portion of the printed circuit board 80 extending outside the housing 60. The interface can provide an enhanced interconnectivity.

The evaluation unit 50 is optionally comprised in the device, e.g., inside the housing 60, on printed circuit board 80, as illustrated. It is also possible to at least partially accomplish the functions of the evaluation unit in an external device, e.g., connected to the device via the interface 85.

Furthermore, we explicitly disclose the following embodiments:

Embodiment 1. A monitoring device for use in lateral flow testing for detecting presence or amount of an analyte in a liquid, the device comprising a housing, the housing comprising a carrier holder for holding a carrier for transport of the liquid;

at least a first light source which is a resonant-cavity light source having a cavity;

an evaluation unit, operationally connected to at least the first light source for detecting a measurement signal;

wherein the first light source is structured and arranged to illuminate with light a test range in a test area of a carrier held in the carrier holder, in particular wherein the illuminating takes place perpendicularly to the test range; and to couple back into the cavity of the first light source a portion of the light coming back from the test range.

Embodiment 2. The monitoring device according to embodiment 1, wherein the evaluation unit comprises an optical detector for detecting an intensity of light emitted by the light source, in particular wherein the measurement signal is derived from the optical detector.

Embodiment 3. The monitoring device according to embodiment 1, wherein the evaluation unit comprises an electrical detector for detecting an electrical supply signal feeding the light source, in particular wherein the measurement signal is derived from the electrical detector.

Embodiment 4. The monitoring device according to one of embodiments 1 to 3, further comprising a mirror disposed in the housing, in particular fixed to a portion of the housing, the mirror being arranged and aligned to reflect light emitted from the first light source having traversed a carrier held in the carrier holder back to the carrier to traverse the carrier again.

Embodiment 5. The monitoring device according to one of embodiments 1 to 4, further comprising at least a first lens disposed in the housing, in particular fixed to a portion of the housing, more particularly fixed to the first light source, the first lens being arranged on an optical path of the light emitted from the first light source towards a carrier held in the carrier holder between the first light source and a carrier held in the carrier holder.

Embodiment 6. The monitoring device according to embodiment 5, wherein first lens is structured and arranged for producing from the light emitted from the first light source a parallelized light beam, in particular wherein the first light source emits the light through a first end mirror of the cavity, and the lens is a convex lens being arranged at a distance from the first end mirror corresponding to a focal length of the first lens.

Embodiment 7. The monitoring device according to one of embodiments 1 to 6, further comprising a printed circuit board held by the housing, on which at least the first light source is mounted, in particular wherein the printed circuit board is aligned parallel to a carrier when the carrier is held in the carrier holder.

Embodiment 8. The monitoring device according to one of embodiments 1 to 7, further comprising a second light source, in particular wherein the second light source is structured and arranged to illuminate with light a control range in a control area of a carrier held in the carrier holder; and to couple back into the cavity of the second light source a portion of the light coming back from the control range.

Embodiment 9. The monitoring device according to one of embodiments 1 to 8, further comprising a third light source, in particular wherein the third light source is structured and arranged to illuminate with light a reference range in a reference area of a carrier held in the carrier holder; and to couple back into the cavity of the third light source a portion of the light coming back from the reference range.

Embodiment 10. A lateral flow testing device for detecting presence or amount of an analyte in a liquid, comprising a monitoring device according to one of embodiments 1 to 9 and a carrier held in the carrier holder, the carrier comprising a sample pad for application of the liquid;

a conjugate pad providing markers for marking the analyte by bonding to the analyte;

a test area in which analyte bonding agents for specifically bonding to the analyte are fixed to the carrier;

a control area in which marker bonding agents for bonding to the markers are fixed to the carrier;

wherein the carrier is structured such that the liquid is transported, in particular transported by capillary forces, from the sample pad to the conjugate pad, thereafter to the test area and thereafter to the control area; and in particular wherein an illumination direction along which the test range is illuminated with the light is perpendicular to a direction of transport (flow direction) of the liquid in the test range.

Embodiment 11. The lateral flow testing device according to embodiment 10, the carrier further comprising a reference area which is void of bonding agents fixed to the carrier, in particular void of analyte bonding agents and void of marker bonding agents.

Embodiment 12. The lateral flow testing device according to embodiment 10 or 11, the carrier further comprising a mirror, in particular wherein the mirror is a reflective coating.

Embodiment 13. The lateral flow testing device according to one of embodiments 10 to 12, wherein the lateral flow testing device is a lateral flow testing device for detecting presence or amount of an analyte and of a further analyte in a liquid, the conjugate pad providing further markers for marking the further analyte by bonding to the further analyte;

the test area comprising a test region in which the analyte bonding agents for specifically bonding to the analyte are fixed to the carrier, and comprising a further test region in which further analyte bonding agents for specifically bonding to the further analyte are fixed to the carrier;

the control area comprising a control region in which the marker bonding agents for bonding to the markers are fixed to the carrier, and comprising a further control region in which further marker bonding agents for bonding to the further markers are fixed to the carrier;

wherein the test range is located in the test region; and the lateral flow testing device comprising a second light source which can be identical with or different from the first light source and which is structured and arranged to illuminate with light a control range in the control region;

to couple back into the cavity of the second light source a portion of the light coming back from the control range;

the lateral flow testing device comprises a further first light source and a further second light source, both being resonant-cavity light sources and having a cavity each, wherein the further second light source can be identical with or different from the further first light source, wherein the further first light source is structured and arranged to illuminate with light a further test range in the further test; and to couple back into the cavity of the further first light source a portion of the light coming back from the further test range; and wherein the further second light source is structured and arranged to illuminate with light a further control range in the further control region; and to couple back into the cavity of the further second light source a portion of the light coming back from the further control range.

Embodiment 14. A method for detecting presence or amount of an analyte in a liquid by lateral flow testing, the method comprising illuminating a test range in a test area of a carrier with light from a first light source which is a resonant-cavity light source having a cavity, in particular wherein the illuminating takes place perpendicularly to the test range; and coupling back into the cavity of the first light source a portion of the light coming back from the test range;

detecting a measurement signal by means of an evaluation unit which is operationally connected to the first light source.

Embodiment 15. The method according to embodiment 14, wherein the carrier comprises a sample pad;

a conjugate pad providing markers for marking the analyte by bonding to the analyte;

a test area in which analyte bonding agents for specifically bonding to the analyte are fixed to the carrier;

a control area in which marker bonding agents for bonding to the markers are fixed to the carrier;

the method comprising letting the carrier transport the liquid from the sample pad to the control area, in particular by capillary forces;

applying the liquid to the sample pad;

letting the markers bond to the analyte at the conjugate pad;

letting the analyte bonding agents bond to the analyte at the test area;

letting the marker bonding agents bond to the markers at the control area; and in particular wherein the method can comprise that the illuminating of the test range with the light takes place along an illumination direction which is perpendicular to a direction of transport (flow direction) of the liquid in the test range.

Embodiment 16. The method according to embodiment 15, further comprising illuminating a control range in the control area with light from a second light source which is a resonant-cavity light source having a cavity, in particular wherein the illuminating of the control range with the light takes place along an illumination direction which is perpendicular to a direction of transport (flow direction) of the liquid in the control range; and coupling back into the cavity of the second light source a portion of the light coming back from the control range;

wherein the second light source is operationally connected to the evaluation unit for detecting a control measurement signal by means of an evaluation unit.

Embodiment 17. The method according to one of embodiments 14 to 16, wherein the carrier comprises a reference area which is void of bonding agents fixed to the carrier, the method further comprising illuminating a reference range in the reference area with light from a third light source which is a resonant-cavity light source having a cavity, in particular wherein the illuminating of the reference range with the light takes place along an illumination direction which is perpendicular to a direction of transport (flow direction) of the liquid in the reference range; and coupling back into the cavity of the third light source a portion of the light coming back from the reference range;

wherein the third light source is operationally connected to the evaluation unit for detecting a reference measurement signal by means of an evaluation unit, in particular wherein the method comprises evaluating by means of the evaluation unit the measurement signal in dependence of the reference measurement signal.

Embodiment 18. A method for detecting presence or amount of a substance in a test range, the method comprising illuminating the test range with light emitted from a resonant-cavity light source having a cavity, in particular wherein the illuminating takes place perpendicularly to the test range;

coupling back into the cavity, light coming back from the test range;

thereby producing a change in a generation of light in the light source, in particular due to interference between the coupled-back light and light being generated in the light source;

monitoring a measurement signal of the light source related to the change.

Embodiment 19 The method according to embodiment 18, comprising letting the substance, if present in the test range, absorb a portion of the light illuminating the test range.

Embodiment 20. The method according to embodiment 18 or 19, wherein the light emitted from the resonant-cavity light source comprises a wavelength which is comprised in an absorption band of the substance.

Embodiment 21. A method for detecting or determining an absorption in a test range, the method comprising illuminating the test range with light emitted from a resonant-cavity light source having a cavity in particular wherein the illuminating takes place perpendicularly to the test range;

coupling back into the cavity, light coming back from the test range;

thereby producing a change in a generation of light in the light source, in particular due to interference between the coupled-back light and light being generated in the light source;

monitoring a measurement signal of the light source related to the change.

Embodiment 22. A device for detecting presence or amount of a substance in a test range, comprising a resonant-cavity light source for illuminating the test range with light, wherein the light source, and in particular its outcoupling mirror, is suited for coupling back into a cavity of the light source, light coming back from the test range;

an evaluation unit for monitoring a measurement signal of the light source related to changes in a generation of light in the light source originating from interference between the coupled-back light and light being generated in the light source.

Embodiment 23. The device according to embodiment 22, wherein the evaluation unit is operable to monitor at least one of an electrical supply signal feeding the light source;

an intensity of the light emitted from the light source.

Embodiment 24. A device for detecting or determining an absorption in a test range, comprising a resonant-cavity light source for illuminating the test range with light, wherein the light source, and in particular its outcoupling mirror, is suited for coupling back into a cavity of the light source, light coming back from the test range;

an evaluation unit for monitoring a measurement signal of the light source related to changes in a generation of light in the light source originating from interference between the coupled-back light and light being generated in the light source;

in particular wherein the device is configured such that the illuminating takes place perpendicularly to the test range.

Embodiment 25. Use of self-mixing interferometry for determining an absorption, in particular for detecting changes in an absorption, more particularly for determining changes in absorption in lateral flow testing.

Embodiment 26. The use according to embodiment 25, comprising illuminating a substance with light emitted from a light source, letting the light interact with the substance and coupling a portion of the light having interacted with the substance back into the light source; in particular wherein, in case the substance flows along a flow direction, the illuminating takes place along an illumination direction which is aligned perpendicular to the flow direction.

Embodiment 27. The use according to embodiment 26, wherein the absorption at a specific wavelength is determined, and wherein the light emitted from the light source comprises this specific wavelength.

Embodiment 28. The use according to embodiment 26 or 27, wherein an absorption of a substance is determined, and the light has a wavelength in an absorption band of the substance.

Embodiment 29. The use according to one of embodiment 25 to 28, which is a use of self-mixing interferometry for determining absorption, more particularly for determining changes in absorption, in lateral flow testing.

Embodiment 30. The use according to one of embodiments 25 to 29, wherein the self mixing interferometry is used for detecting one or more of an absorption of a substance at a test area of an LFT device;

an absorption of a substance at a control area of an LFT device;

an absorption of a substance at a reference area of an LFT device.

Embodiment 31. Use of self-mixing interferometry for detecting a color intensity, in particular for detecting changes in color intensity, more particularly for detecting changes in color intensity in lateral flow testing.

The invention claimed is:

1. A monitoring device configured to detect a presence or an amount of an analyte in a liquid using lateral flow testing, the monitoring device comprising:

a housing comprising a carrier holder configured to hold a carrier for transport of the liquid;

a first light source which is a resonant-cavity light source having a cavity; and an evaluation unit configured to detect a measurement signal, and being operationally connected to the first light source, wherein the first light source is structured and arranged:

to illuminate with light a test range in a test area of a carrier held in the carrier holder; and to couple back into the cavity of the first light source a portion of the light coming back from the test range.

2. The monitoring device according to claim 1, wherein the evaluation unit comprises an optical detector configured to detect an intensity of light emitted by the first light source, and the measurement signal is derived from the optical detector.

3. The monitoring device according to claim 1, wherein the evaluation unit comprises an electrical detector configured to detect an electrical supply signal feeding the first light source, and the measurement signal is derived from the electrical detector.

4. The monitoring device according to claim 1, further comprising a mirror disposed in the housing, the mirror being arranged and aligned to reflect light emitted from the first light source having traversed a carrier held in the carrier holder back to the carrier to traverse the carrier again.

5. The monitoring device according to claim 4, wherein the mirror is fixed to a portion of the housing.

6. The monitoring device according to claim 1, further comprising a first lens disposed in the housing, the first lens being arranged on an optical path of the light emitted from the first light source towards a carrier held in the carrier holder between the first light source and the carrier held in the carrier holder.

7. The monitoring device according to claim 6, wherein:
the first light source is configured to emit the light through a first end mirror of the cavity, and
the first lens is a convex lens arranged at a distance from the first end mirror corresponding to a focal length of the first lens, the first lens being structured and arranged to produce a parallelized light beam from the light emitted from the first light source.

8. The monitoring device according to claim 6, wherein the first lens is fixed to a portion of the housing or the first light source.

9. The monitoring device according to claim 1, further comprising a printed circuit board held by the housing, on which at least the first light source is mounted.

10. The monitoring device according to claim 9, wherein the printed circuit board is aligned parallel to a carrier when the carrier is held in the carrier holder.

11. The monitoring device according to claim 1, further comprising a second light source structured and arranged:
to illuminate with light a control range in a control area of a carrier held in the carrier holder; and
to couple back into the cavity of the second light source a portion of the light coming back from the control range.

12. The monitoring device according to claim 1, further comprising a third light source structured and arranged:
to illuminate with light a reference range in a reference area of a carrier held in the carrier holder; and
to couple back into the cavity of the third light source a portion of the light coming back from the reference range.

13. A lateral flow testing device configured to detect a presence or an amount of an analyte in a liquid, the lateral flow testing device comprising:
a monitoring device according to claim 1; and
a carrier held in the carrier holder, the carrier comprising:
a sample pad for application of the liquid;
a conjugate pad comprising markers for marking the analyte by bonding to the analyte;
a test area in which analyte bonding agents for specifically bonding to the analyte are fixed to the carrier; and
a control area in which marker bonding agents for bonding to the markers are fixed to the carrier, wherein the carrier is structured such that the liquid is transported from the sample pad to the conjugate pad, thereafter to the test area, and thereafter to the control area.

14. The lateral flow testing device according to claim 13, wherein the carrier further comprises
a reference area which is void of analyte bonding agents and void of marker bonding agents.

15. The lateral flow testing device according to claim 13, wherein the carrier further comprises a mirror.

16. The lateral flow testing device according to claim 15, wherein the mirror is a reflective coating.

17. The lateral flow testing device according to claim 13, further configured to detect a presence or an amount of a further analyte in the liquid using lateral flow testing, wherein:
the conjugate pad further comprises further markers for marking the further analyte by bonding to the further analyte;
the test area comprises a test region in which the analyte bonding agents for specifically bonding to the analyte are fixed to the carrier, wherein the test range is located in the test region, and a further test region in which further analyte bonding agents for specifically bonding to the further analyte are fixed to the carrier; and
the control area comprises a control region in which the marker bonding agents for bonding to the markers are fixed to the carrier, and a further control region in which further marker bonding agents for bonding to the further markers are fixed to the carrier;
the lateral flow testing device further comprising:
a second light source which can be identical with or different from the first light source and which is structured and arranged;
to illuminate with light a control range in the control region; and
to couple back into the cavity of the second light source a portion of the light coming back from the control range,
a further first light source which is a resonant-cavity light source having a cavity, wherein the further first light source is structured and arranged:
to illuminate with light a further test range in the further test region; and
to couple back into the cavity of the further first light source a portion of the light coming back from the further test range; and
a further second light source which is a resonant-cavity light source having a cavity, wherein the further second light source can be identical with or different from the further first light source and is structured and arranged:
to illuminate with light a further control range in the further control region; and
to couple back into the cavity of the further second light source a portion of the light coming back from the further control range.

18. The lateral flow testing device according to claim 13, wherein the carrier is structured such that the liquid is transported by capillary forces from the sample pad to the conjugate pad, thereafter to the test area, and thereafter to the control area.

19. A method for detecting a presence or an amount of an analyte in a liquid by lateral flow testing, the method comprising:
illuminating a test range in a test area of a carrier with light from a first light source which is a resonant-cavity light source having a cavity;

coupling back into the cavity of the first light source a portion of the light coming back from the test range; and detecting a measurement signal by means of an evaluation unit which is operationally connected to the first light source.

20. The method according to claim 19, wherein the carrier comprises:

a sample pad;

a conjugate pad providing markers for marking the analyte by bonding to the analyte;

a test area in which analyte bonding agents for specifically bonding to the analyte are fixed to the carrier; and a control area in which marker bonding agents for bonding to the markers are fixed to the carrier;

the method further comprising:

letting the carrier transport the liquid from the sample pad to the control area;

applying the liquid to the sample pad;

letting the markers bond to the analyte at the conjugate pad;

letting the analyte bonding agents bond to the analyte at the test area; and letting the marker bonding agents bond to the markers at the control area.

\* \* \* \* \*